United States Patent
Balázs et al.

(10) Patent No.: US 9,221,870 B2
(45) Date of Patent: Dec. 29, 2015

(54) CRYSTAL FORM OF AN ORGANIC COMPOUND AND PROCESS FOR THE PREPARATION THEREOF

(75) Inventors: Attila Balázs, Kerepes (HU); János Csörgei, Budapest (HU); Ádám Demeter, Budapest (HU); Csaba Sánta, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 49 days.

(21) Appl. No.: 13/387,783

(22) PCT Filed: Aug. 5, 2010

(86) PCT No.: PCT/HU2010/000088
§ 371 (c)(1),
(2), (4) Date: Feb. 21, 2012

(87) PCT Pub. No.: WO2011/015892
PCT Pub. Date: Feb. 10, 2011

(65) Prior Publication Data
US 2012/0142655 A1    Jun. 7, 2012

(30) Foreign Application Priority Data
Aug. 5, 2009 (HU) ..................... 0900487

(51) Int. Cl.
| A61K 31/573 | (2006.01) |
| A61P 35/00  | (2006.01) |
| C07J 7/00   | (2006.01) |
| C07J 41/00  | (2006.01) |

(52) U.S. Cl.
CPC .................. C07J 41/0083 (2013.01)

(58) Field of Classification Search
USPC .......................... 514/181; 552/595
See application file for complete search history.

(56) References Cited

U.S. PATENT DOCUMENTS

| 6,768,014 | B2 * | 7/2004  | Kim et al.    | 552/595 |
| 6,861,415 | B2 * | 3/2005  | Kim et al.    | 514/179 |
| 6,900,193 | B1 * | 5/2005  | Kim et al.    | 514/179 |
| 8,044,223 | B2 * | 10/2011 | VanRheenen    | 552/595 |
| 8,173,626 | B2 * | 5/2012  | Hausknecht    | 514/179 |
| 8,183,402 | B2 * | 5/2012  | Bodi et al.   | 552/595 |
| 2012/0077791 | A1 | 3/2012 | Santa et al. | |

FOREIGN PATENT DOCUMENTS

| WO | WO9741145 A1    | 11/1997 |
| WO | WO0147945 A1    | 7/2001  |
| WO | WO0174840 A2    | 10/2001 |
| WO | WO2004089970 A2 | 10/2004 |
| WO | WO2008088935 A2 | 7/2008  |
| WO | WO2009001148 A2 | 12/2008 |
| WO | WO2009134725 A2 | 11/2009 |
| WO | WO2010106383 A8 | 9/2010  |

OTHER PUBLICATIONS

Van Rheenen et al. (AN 2004:872872, HCAPLUS, 141:366370 abstract of WO 2004089970).*
STN Search Registry of compound CDB 4124.*
International Preliminary Report on Patentability and Written Opinion; Feb. 7, 2012; World Intellectual Property Organization (WIPO) (International Bureau Of); PCT/HU2010/000088; 8 pages.
International Search Report; Feb. 9, 2011; World Intellectual Property Organization (WIPO) (International Bureau Of); PCT/HU2010/000088; 3 pages.

* cited by examiner

Primary Examiner — Sabiha N Qazi
(74) Attorney, Agent, or Firm — Fish & Richardson P.C.

(57) ABSTRACT

The present invention relates to novel crystalline Form II of 17α-acetoxy-21-methoxy-11β-[4-N,N-dimethylaminophenyl]-19-norpregna-4,9-diene-3,20-dione, (also known as CDB-4124), processes for the preparation thereof and pharmaceutical compositions comprising it. Form II can be crystallized from different medium such as esters of C1-C4 alcohols and carboxylic acids, ketones, cyclohexane, acetonitrile, dimethylformamide, dimethyl sulfoxide, water and any mixture thereof.

9 Claims, 4 Drawing Sheets

CRYSTAL FORM OF AN ORGANIC COMPOUND AND PROCESS FOR THE PREPARATION THEREOF

CROSS-REFERENCE TO RELATED APPLICATIONS

This application is a National Stage application under 35 U.S.C. §371 and claims the benefit under 35 U.S.C. §119(a) of International Application No. PCT/HU2010/000088, having an International Filing Date of Aug. 5, 2010, which claims the benefit of priority of Hungary Application Serial Number P0900487, having a filing date of Aug. 5, 2009, all of which are incorporated by reference herein in their entirety.

FIELD OF THE INVENTION

The present invention relates to novel crystalline Form II of 17α-acetoxy-21-methoxy-11β-[4-N,N-dimethylaminophenyl]-19-norpregna-4,9-diene-3,20-dione, (also known as CDB-4124), processes for the preparation thereof and pharmaceutical composition comprising it.

BACKGROUND OF THE INVENTION

17α-acetoxy-21-methoxy-11β-[4-N,N-dimethylaminophenyl]-19-norpregna-4,9-diene-3,20-dione) is a selective progesterone receptor modulator, it is tested for treatment of progesterone sensitive myomata.

International patent application WO 97/41145 disclosed first time the preparation of 17α-acetoxy-21-methoxy-11β-[4-N,N-dimethylaminophenyl]-19-norpregna-4,9-diene-3,20-dione). In example 9 it is characterized as light-yellow powder with a melting point of 116° C. (purity: 98.06%, characteristic FT-IR absorption bands at: 1124, 1235, 1370, 1446, 1518, 1612, 1663, 1734, 2940 cm$^{-1}$).

According to WO 01/47945 and WO 01/74840 published international patent applications, the obtained 17α-acetoxy-21-methoxy-11β-[4-N,N-dimethylaminophenyl]-19-norpregna-4,9-diene-3,20-dione) was light-yellow powder as well having a melting point of 116° C. (purity: 98.87%, 98.06%, characteristic FT-IR absorption bands at: 1124, 1235, 1370, 1446, 1518, 1612, 1662, 1734, 2940 cm$^{-1}$)

Final products of the above mentioned procedures were obtained by expensive purification processes. First, the crude product was purified by chromatography then after evaporation the obtained foam was treated in ultrasonic cleaner.

International patent application WO 2009001148 discloses another preparation process wherein the final product is obtained by chromatographic purification and evaporation (impurity: 0.5%, melting point: 118° C., solid-state characteristics determined by analytical technology are shown in FIG. 1-4).

Using preparation processes known in the literature, we have found that the products could not crystallize spontaneously. The purification of the crude product is expensive, difficult and not efficient enough. As the product can not be crystallized, which is the most efficient purification procedure, therefore, more difficult and expensive cleaning processes must be applied (for example chromatographic purification). The amorphous product has small grain size so the filtration thereof is quite difficult. On the one part, the unsuitable chemical stability of the amorphous form makes the drying and the storage of the product uneasy, and on the other part, the grain size and electrostatical properties of this form makes the blending, packing, sampling etc. difficult.

It must be emphasized that the pharmaceutical utility of a compound depends on the purity of the final product. To develop a reproducible large-scale preparation it is very important to obtain a product which can be filtered and dried easily. From this point of view it is also important for the product to remain stable for a long time without using any special storage conditions.

From a pharmaceutical point of view, the use of the amorphous product obtained by the above-mentioned procedures is not economical and very difficult. Thus, it is necessary to develop a process to obtain a pure crystalline product, because on the one hand, it ensures suitable pharmaceutical properties, and on the other hand, reduces the cost of the purification process significantly.

Hungarian patent application P090171 disclosed the preparation of crystalline Form A of CDB-4124. The final product was obtained by chromatographic purification of amorphous CDB-4124 followed by a crystallization process. The melting point of the product is 166-168° C. The solid-sate characteristic of anhydrate Form A was determined by IR, Raman, X-ray powder diffraction, $^{13}$C solid-state NMR measurements.

The crystalline form is unambiguously more advantageous than the amorphous form, due to its better chemical and physical stability.

In view of the pharmaceutical value of a compound, it is of prime importance to obtain it with excellent purity. It is also important to be able to synthetize it by means of a process that can readily be converted to industrial scale, especially in a form that allows rapid filtration and drying. From the above technological and product quality point of view, certain polymorphs, via a specific synthetic route, provide unique opportunity to fulfill these requirements. Therefore, there is a pharmaceutical need to find proper polymorphs and crystallization process that advantageously provides a compound in excellent purity with rapid filtration and drying properties in an industrial scale. Long-lasting, good stability without using special storage conditions is an important requirement as well.

As it is known, the less stable polymorphic form of a compound can transform into a more stable form thereof. Therefore, there is a need to find the most stable polymorphic form to avoid the polymorphic transformation, because transformation of the active ingredient may change the dissolution profile and the bioavailability of the pharmaceutical composition. Several examples are known when marketed drugs had to be withdrawn temporarily due to polymorphic transformation of the active ingredient. In order to launch them again, more development was needed and it had a considerable cost.

It has now been discovered that a more stable crystalline form of 17α-acetoxy-21-methoxy-11β-[4-N,N-dimethylaminophenyl]-19-norpregna-4,9-diene-3,20-dione) can be prepared.

SUMMARY OF THE INVENTION

The present invention relates to a chemically and physically stable new crystalline form of CDB-4124 and preparation thereof and pharmaceutical composition containing it.

DETAILED DESCRIPTION OF THE INVENTION

The present invention relates to the chemically and physically stable crystalline Form II of CDB-4124 and the preparation thereof. According to the state of the art, this form is the thermodynamically most stable polymorphic form.

While crystallizing CDB-4124 from a different medium, we have surprisingly found that a new crystalline form can be obtained. Crystalline Form II of CDB-4124 is more stable than the already known polymorphs of CDB-4124 (amorphous form, crystalline Form I) are and has a higher melting point. The melting point of the high purity crystalline Form II of CDB-4124 is 201-204° C., which is significantly higher than that of crystalline Form I (166-168° C.).

Form II can be crystallized from different medium such as esters of C1-C4 alcohols and carboxylic acids, ketones, cyclohexane, acetonitrile, dimethylformamide, dimethyl sulfoxide, water and any mixture thereof.

In accordance with the present invention, it has been found that the anhydrate Form II of CDB-4124 can be produced as follows:

Dissolving the basic substance at between 0° C.-40° C.—advantageously at room temperature—in 1-50 times larger amount of a solvent—advantageously 2-10 times larger—selected from esters of C1-C4 alcohols and carboxylic acids, ketones, cyclohexane, acetonitrile, dimethylformamide, dimethyl sulfoxide, water and any mixture thereof. Solution concentration suitable for crystallization may be controlled by evaporation. Crystallization is carried out at between −20° C.-40° C., advantageously at between −5° C.-25° C. Seed crystal may be added to solution in order to help or increase the speed of crystallization.

Crystalline Form II may also be prepared by dissolving crystalline Form I or the amorphous form of CDB-4124 in 2-10 times larger amount of any of the above mentioned water-mixable solvents at between 0-40° C. and then precipitating the product with 20-100 times larger amount of water.

After filtration of precipitated crystals, the product is dried in order to eliminate the solvents.

Form I is a monotropic modification of CDB-4124 such as Form II. Crystalline Form II is thermodynamically more stable at any temperature. It is proved by its higher melting point and worse solubility at 25° C. in different solvents (MeOH: 500 mg/ml Form I, 23 mg/ml Form II). Furthermore, Form I can be transformed into Form II via crystallization from different medium.

The crystalline Form II of CDB-4124 is suitable for manufacturing various pharmaceutical formulations—advantageously tablets and capsules—with pharmaceutically acceptable ingredients.

The solid-state characteristics of anhydrate Form II of CDB-4124 determined by suitable analytical techniques are disclosed below.

The most characteristic XRPD reflections are the following: 6.8, 11.0, 11.6 14.9, 19.1 [°]±0.2 [°] 2θ.

Characteristic XRPD peaks are shown in Table 1:

TABLE 1

| No. | Angle 2Θ | Rel. int. (%) |
|---|---|---|
| 1 | 6.4 | 2 |
| 2 | 6.8 | 15 |
| 3 | 8.7 | 14 |
| 4 | 9.3 | 6 |
| 5 | 11.0 | 37 |
| 6 | 11.6 | 78 |
| 7 | 12.9 | 7 |
| 8 | 13.4 | 28 |
| 9 | 14.9 | 36 |
| 10 | 16.1 | 21 |
| 11 | 16.5 | 21 |
| 12 | 17.0 | 34 |
| 13 | 17.5 | 13 |
| 14 | 17.8 | 17 |
| 15 | 18.0 | 14 |
| 16 | 18.2 | 3 |
| 17 | 18.8 | 20 |
| 18 | 19.1 | 100 |
| 19 | 19.9 | 45 |
| 20 | 20.2 | 16 |
| 21 | 20.7 | 21 |
| 22 | 21.5 | 26 |
| 23 | 21.7 | 8 |
| 24 | 22.1 | 26 |
| 25 | 22.4 | 21 |
| 26 | 23.3 | 29 |
| 27 | 23.8 | 5 |
| 28 | 24.2 | 50 |
| 29 | 24.5 | 10 |
| 30 | 25.1 | 18 |
| 31 | 25.4 | 26 |
| 32 | 26.3 | 13 |
| 33 | 27.2 | 23 |
| 34 | 27.9 | 28 |
| 35 | 28.7 | 10 |
| 36 | 28.9 | 9 |
| 37 | 29.5 | 6 |
| 38 | 29.7 | 6 |
| 39 | 30.6 | 3 |
| 40 | 31.1 | 8 |

Figure 1:
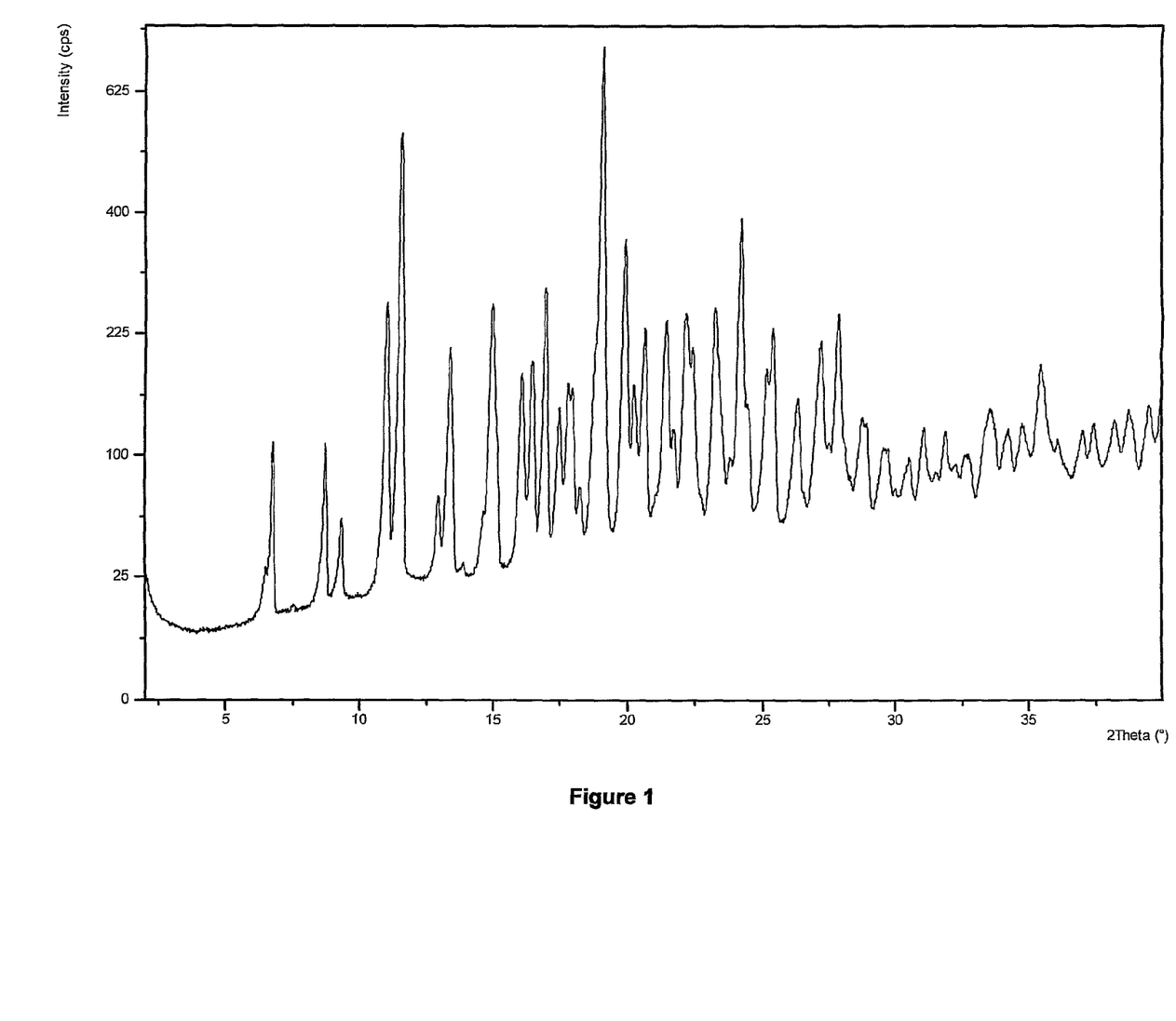
FIG. 1: X-Ray Powder Diffraction pattern of anhydrate crystalline Form II of CDB-4124

The characteristic X-ray powder diffraction pattern is shown in FIG. 1.

The most characteristic Raman absorption bands of CDB-4124 anhydrate Form II are the following: 3054, 2963, 2850, 1604, 1195, 1159±4 cm$^{-1}$.

Further characteristic Raman absorption bands of CDB-4124 anhydrate Form II are at: 3069, 3054 2963, 2889, 2850, 1730, 1661, 1604, 1442, 1383, 1306, 1275, 1214, 1195, 1159, 1015, 790, 441±4 cm$^{-1}$.

Figure 2:
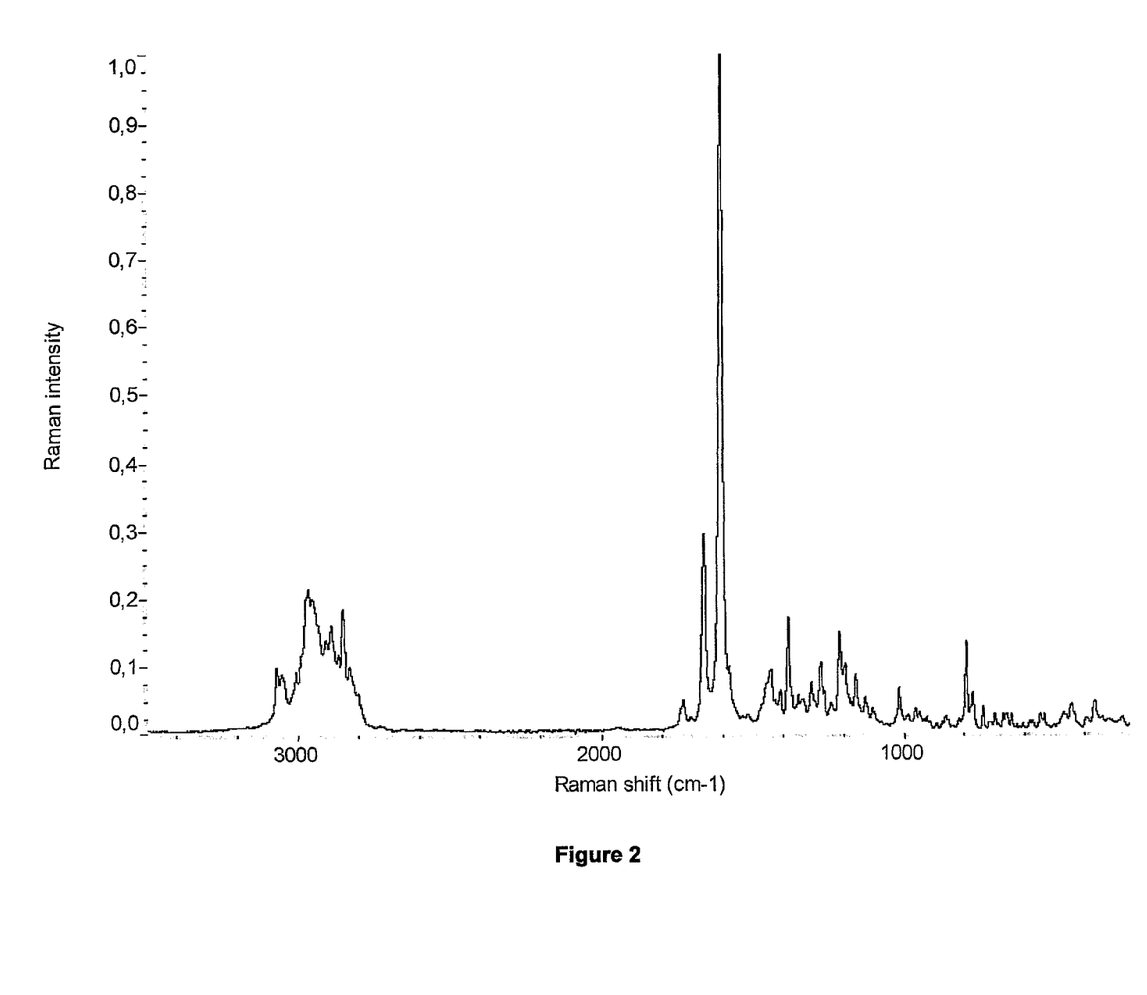
FIG. 2: FT-Raman spectrum of anhydrate crystalline Form II of CDB-4124

The characteristic Raman spectrum is shown in FIG. 2.

The most characteristic resonances in $^{13}C$ solid-state NMR spectrum of CDB-4124 anhydrate Form A are the following: 196.7, 172.4, 169.3, 20.7, 20.1, 17.7±0.1 ppm.

Resonances in $^{13}C$ solid-state NMR spectrum of CDB-4124 anhydrate Form II are at: 202.1, 200.9, 196.7, 172.4, 169.3, 155.2, 152.8, 150.2, 149.4, 144.6, 142.6, 133.9, 130.5, 129.8, 129.2, 127.7, 126.6, 123.0, 114.3, 112.8, 111.4, 96.9, 91.7, 77.3, 75.7, 60.3, 59.0, 54.1, 49.8, 47.9, 42.1, 39.5, 38.1, 37.1, 35.4, 33.0, 32.0, 31.1, 29.2, 27.8, 26.1, 25.1, 24.5, 20.7, 20.1, 17.7, 14.9±0.1 ppm.

Figure 3:
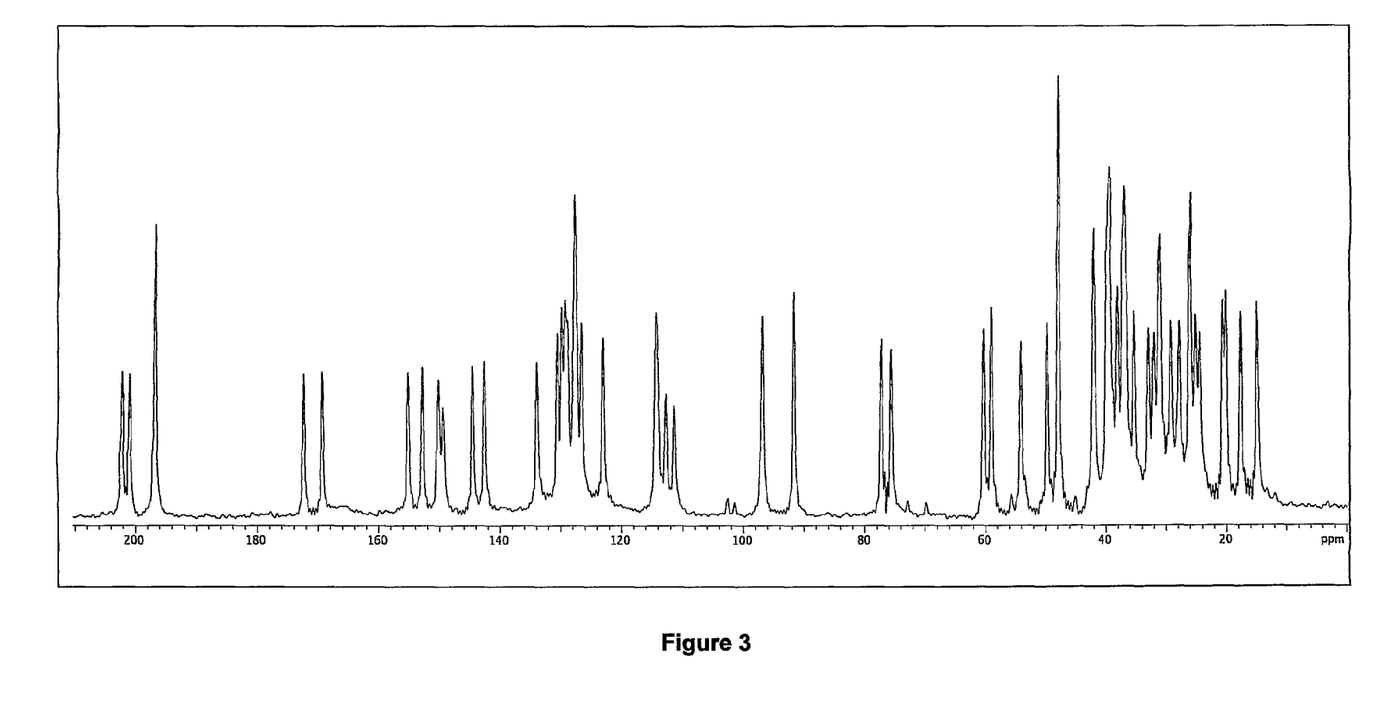
FIG. 3: $^{13}C$ CP/MAS solid-state NMR spectrum of anhydrate crystalline Form II of CDB-4124

The characteristic $^{13}C$ CP/MAS solid-state NMR spectrum is shown in FIG. 3.

It has now been discovered that anhydrate Form II is the thermodynamically most stable polymorph of CDB-4124. It has a well-defined columnar structure. Form II has advantageous filtering and drying properties and very good flowing properties as well.

The crystallization process according to the invention provide a compound in excellent purity with good handling and technological properties. These properties permit to develop a more economical purification process for large-scale production as well.

The following investigations were completed to compare the most important pharmaceutical properties of the chromatographically purified amorphous product and the crystalline product.

Fast Stability Test

Amorphous and crystalline forms were stored on a plate at 40° C. in the presence of air for 10 days. Impurity was measured at different times using an HPLC equipment. The largest degradation product was the N-methyl derivative of CDB-4124. Results of the purity examination shows that the stability of crystalline form is much better than that of the amorphous form. Considering that a less stable solid form can potentially turn into a more stable form, this property is clearly an advantage in pharmaceutical development. The results are shown in Table 2 below.

TABLE 2

|  | Amorphous form | | Form II | |
|---|---|---|---|---|
|  | Impurity | N-demethyl-derivative of CDB-4124 | Impurity | N-demethyl-derivative of CDB-4124 |
| Day 0 | 0.87% | 0.15% | 0.14% | 0.02% |
| Day 1 | 0.97% | 0.21% | 0.14% | 0.02% |
| Day 2 | 1.03% | 0.25% | 0.14% | 0.02% |
| Day 6 | 1.63% | 0.55% | 0.15% | 0.02% |
| Day 10 | 1.97% | 0.73% | 0.17% | 0.03% |
| Σ | 1.1% | 0.58% | 0.03% | 0.01% |

Effect of Crystallization on Purification of the Product

The crude product was crystallized from various solvents. Impurity of the crystalline product was measured by HPLC. The results are shown in Table 3 below.

TABLE 3

|  | Crude product | Form II (crystallized from acetone) | Form II (crystallized from ethyl-acetate) | Form II (crystallized from acetonitrile) |
|---|---|---|---|---|
| Impurity | 8.54% | 3.07% | 2.26% | 1.62% |

These results have proved that the crystallization of the crude product from various solvents provided a much better compound purity. Consequently, crystallization process can be applied advantageously to purify the crude product.

Investigation of Water Adsorption Properties

From the examination of water adsorption properties, important conclusions can be made about the physical and chemical stability of a compound. Amorphous compounds can adsorb more water from the air. This property is deliberately disadvantageous during the preparation process of a pharmaceutical composition, since the real amount of the active ingredient can't be measured because of the adsorbed water.

Figure 4:
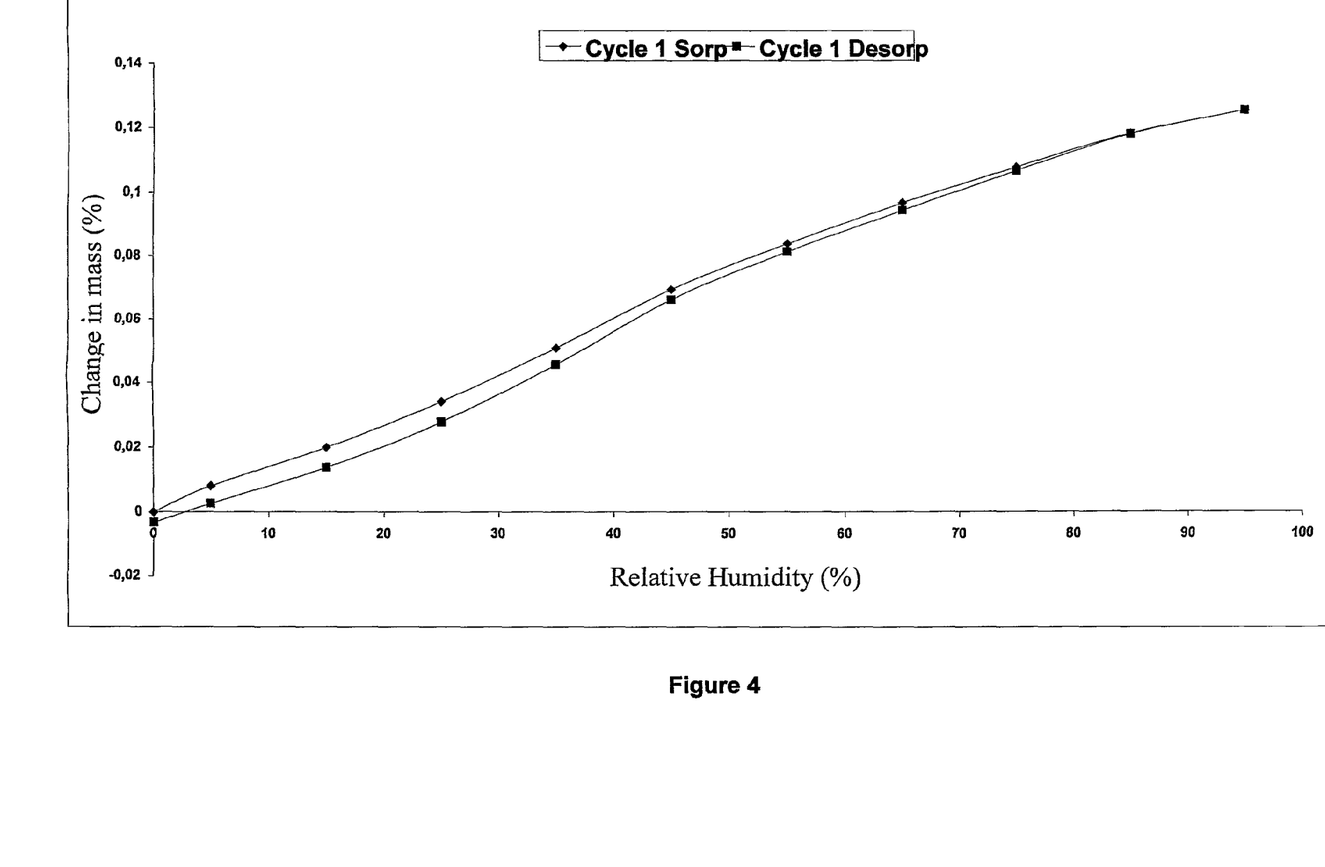
FIG. 4: Water Vapour Sorption Isotherm of anhydrate crystalline Form II of CDB-4124

Water adsorption properties of the crystalline Form II of CDB-4124 were measured by dynamic vapour sorption technique (DVS). Water vapour sorption isotherm of crystalline Form II CDB-4124 (adsorption-desorption) is shown in FIG. 4. As the degree of humidity was increased, the mass of the crystalline Form II of CDB-4124 barely changed, the water was adsorbed by its surface and this interaction is reversible.

As mentioned above, this property of crystalline CDB-4124 is advantageous during technological processes relating to the formulating of the pharmaceutical composition, because water adsorption can't falsify the measurement of the real amount of the active substance.

The examination also proves that Form II is a stable anhydrate at room-temperature, independently of a change in relative humidity.

Applied Measuring Conditions:
Parameters of FT-Raman Spectral Measurements:
Spectrometer: Thermo-Nicolet NXR-9650
Sample holder: MicroStage™, 50 μm lateral laser beam
Spectral range: 3500-200 cm$^{-1}$
Spectral resolution: 4 cm$^{-1}$
Scan number: 128
Exciting power: 300 mW
Parameters of X-Ray Powder Diffraction Measurements:
Diffractometer: PANanalytical X'Pert PRO MPD
Radiation: CuK$_\alpha$
Accelerating voltage: 40 kV
Anode current: 40 mA
Goniometer: PW3050/60
Detector: PIXcel (PW3018/00)
Scanning rate: 0.03°2θ/s
Step size: 0.01°2θ
Measuring range: 2-40°2θ
Sample holder: PW1811/16 (reflection, back loading)
Spinner of sample holder: PW3064/60 (reflection/transmission spinner)
Speed of spinning: 1 revolution/s
Measuring sensitivity: ±0.2°2θ
Parameters of DVS Measurements:
Instrument: SMS DVS Advantage 1
dm/dt: 0.002%/min
Temperature: 25° C.
Humidity profile: 0%-95% relative humidity in steps of 10% (adsorption-desorption)
Nitrogen purge gas: 200 ml/min
Solvent: water
Parameters of $^{13}$C CP/MAS Solid-State NMR Measurements:
Instrument: Varian NMR System 600 MHz (14.1 Tesla) VnmrJ 2.2C
Probe: 3.2 mm HX
Experiment: $^{13}$C CPMAS (tancpx)
Speed of spinning: 15 kHz
Rotor: 3.2 mm thin-wall zirkonia
Temperature: 25° C.
Cross-polarisation time: 3 ms (CP)
Relaxation delay: 10 s
Reference: CH$_2$ signal of adamantine at 38.5 ppm
Number of retries: 512

EXAMPLES

The following examples are merely illustrative of the present invention and should not be construed as limiting the scope of the invention in any way as many variations and equivalents that are encompassed by present invention will become apparent to those skilled in the art upon reading the present disclosure.

Example 1

4.8 g of amorphous CDB-4124 was dissolved in the mixture of 5 ml ethyl-acetate and 5 ml cyclohexane, then the solution was stirred in nitrogen atmosphere at 20-25° C. After dissolution it started to crystallize. For one hour the solution was stirred then the precipitated crystals were filtered and dried at 25° C. to yield 3.65 g crystalline Form II of CDB-4124. The X-ray diffraction pattern of the product is identical with the pattern in FIG. 1.

Example 2

1.0 g of crystalline Form I (described in P090171) was dissolved in 20 ml of methanol, then the solution was stirred in nitrogen atmosphere at 20-25° C. After dissolution, it started to crystallize. If the crystallization, didn't begin in 1 hour, a seed crystal was added to the solution (Example 1). After the beginning of crystallization the mixture was stirred for 25-30 minutes at 20-25° C. The precipitated crystals were filtered and dried at 25° C. to yield 0.64 g of crystalline Form II of CDB-4124.

The X-ray diffraction pattern of the product is identical with the pattern in FIG. 1.

Example 3

3400 l of chromatographically purified solution of CDB-4124 comprising 20.6 kg of the active ingredient (portion of solvents: cyclohexane:ethyl-acetate:1:1, degree of concentration: 5-7 g/l) was evaporated (film evaporator) in two portions at 20-35° C. to obtain 400-500 l of the solution. After evaporation the precipitation began. Then the solution was further evaporated in acid resistant autoclave until the volume of the suspension was less than 150 l. Methanol was added to the solution, then it was distilled repeatedly until the content of the ethyl-acetate was less than 10%. The suspension was evaporated again to obtain 50-70 l then it was cooled down below −8° C. and was stirred for 8 hours. The precipitated crystals were filtered and washed with methanol (5-10 l, −10±2° C.), then it was dried under vacuum at 25-35° C. to yield 14.7 kg of crystalline Form II of CDB-4124.

The X-ray diffraction pattern of the product is identical with the pattern in FIG. 1.

Example 4

5000 l of chromatographically purified solution of CDB-4124 comprising 33.9 kg of the active ingredient (portion of solvents: cyclohexane:ethyl-acetate:1:1, degree of concentration: 5-7 g/l) was evaporated (film evaporator) at 20-35° C. to obtain 800-900 l of the solution (until the precipitation began). Then the solution was further evaporated in acid resistant autoclave until the volume of the suspension was less than 300 l. Evaporations were carried out under vacuum at 25-35° C. until the volume of the suspension was less than 150 l and it was still stirable. Then 100±20 kg cyclohexane was added to the suspension at 20-25° C. and it was cooled down to −10±2° C. The suspension was stirred for 2 hours, then the precipitated crystals were filtered and washed with the mixture of cylohexane and ethyl-acetate (1:3, 20-25 l, −10±2° C.), then it was dried under vacuum at 25-35° C. to yield 27.1 kg of crystalline Form II of CDB-4124.

The X-ray diffraction pattern of the product is identical with the pattern in FIG. 1.

Example 5

3.0 g of CDB-4124 was dissolved in 20 ml of acetonitrile, the solution was evaporated to half its original volume then it was stirred in nitrogen atmosphere for 1 hour at 20-25° C. If the crystallization didn't begin in 1 hour, a seed crystal was added to the solution (Example 1). The suspension was cooled down to 0-5° C., then it was stirred for 1 hour. The precipitated crystals were filtered and dried at 25° C. to yield 1.19 g of crystalline Form II of CDB-4124. The X-ray diffraction pattern of the product is identical with the pattern in FIG. 1.

Example 6

3.0 g of CDB-4124 was dissolved 13 ml of ethyl-acetate, then it was stirred in nitrogen atmosphere for 1 hour at 20-25° C. If the crystallization didn't begin in 1 hour, a seed crystal was added to the solution (Example 1). The suspension was cooled down to 0-5° C. then it was stirred for 1 hour. The precipitated crystals were filtered and dried at 25° C. to yield 1.78 g of crystalline Form II of CDB-4124.

The X-ray diffraction pattern of the product is identical with the pattern in FIG. 1.

Example 7

2.0 g amorphous CDB-4124 was dissolved in 20 ml of acetone in inert gas atmosphere at 20-25° C. while the solution was stirred. The obtained solution was added to cleared water while it was stirred, thereafter, it was stirred for another 30 minutes at 20-25° C. If the crystallization didn't begin in 1 hour, a seed crystal was added to the solution (Example 1). The precipitated crystals were filtered, washed with water and dried at 25° C. to yield 0.96 g of crystalline Form II of CDB-4124.

The X-ray diffraction pattern of the product is identical with the pattern in FIG. 1.

Example 8

1000 Capsules

| Ingredient | Weight (g) | Percentage composition by weight (m/m %) |
| --- | --- | --- |
| CDB-4124 | 25 | 12.5 |
| Microcrystalline cellulose | 49.5 | 24.75 |
| Lactose | 123.5 | 61.75 |
| Magnesium stearate | 2 | 1 |

The above listed ingredients were homogenized, then filled into hard gelatine capsules. Capsule fill weight was 200 mg and each capsule contained 25 mg of the active ingredient.

Example 9

1000 Capsules

| Ingredient | Weight (g) | Percentage composition by weight (m/m %) |
| --- | --- | --- |
| CDB-4124 | 50 | 12.5 |
| Microcrystalline cellulose | 99 | 24.75 |
| Lactose | 247 | 61.75 |
| Magnesium stearate | 4 | 1 |

The above listed ingredients were homogenized, then filled into hard gelatine capsules. Capsule fill weight was 400 mg and each capsule contained 50 mg of the active ingredient.

Example 10

1000 Capsules

| Ingredient | Weight (g) | Percentage composition by weight (m/m %) |
|---|---|---|
| CDB-4124 | 25 | 12.5 |
| Microcrystalline cellulose | 171 | 85.5 |
| Magnesium stearate | 4 | 2 |

The above listed ingredients were homogenized, then filled into hard gelatine capsules. Capsule fill weight was 200 mg and each capsule contained 25 mg of the active ingredient.

Example 11

1000 Capsules

| Ingredient | Weight (g) | Percentage composition by weight (m/m %) |
|---|---|---|
| CDB-4124 | 50 | 12.5 |
| Microcrystalline cellulose | 342 | 85.5 |
| Magnesium stearate | 8 | 2 |

The above listed ingredients were homogenized, then filled into hard gelatine capsules. Capsule fill weight was 400 mg and each capsule contained 50 mg of the active ingredient.

The invention claimed is:

1. A crystalline anhydrate Form II of 17α-acetoxy-21-methoxy-11β-[4-N,N-dimethylaminophenyl]-19-norpregna-4,9-diene-3,20-dione characterized in that it provides one or more of:
   a) a characteristic X-ray powder diffractions with peaks at 6.8, 11.0, 11.6, 14.9, 19.1±0.2 [°]2θ;
   b) a characteristic FT Raman absorption bands at 3054, 2963, 2850, 1604, 1195, 1159±4 cm$^{-1}$; and
   c) a $^{13}$C solid-state NMR spectrum comprising characteristic resonances at 196.7, 172.4, 169.3, 20.7, 20.1, 17.7±0.1 ppm.

2. A crystalline anhydrate Form II of 17α-acetoxy-21-methoxy-11β-[4-N,N-dimethylaminophenyl]-19-norpregna-4,9-diene-3,20-dione according to claim 1 characterized in that it has an X-ray powder diffraction pattern as shown in FIG. 1.

3. A crystalline anhydrate Form II of 17α-acetoxy-21-methoxy-11β-[4-N,N-dimethylaminophenyl]-19-norpregna-4,9-diene-3,20-dione according to claim 1 characterized in that it has an FT Raman spectrum as shown in FIG. 2.

4. A crystalline anhydrate Form II of 17α-acetoxy-21-methoxy-11β-[4-N,N-dimethylaminophenyl]-19-norpregna-4,9-diene-3,20-dione according to claim 1 characterized in that it has a $^{13}$C solid-state NMR spectrum in accordance with FIG. 3.

5. A process for preparing a crystalline anhydrate Form II of 17α-acetoxy-21-methoxy-11β-[4-N,N-dimethylaminophenyl]-19-norpregna-4,9-diene-3,20-dione according to claim 1 wherein the amorphous 17α-acetoxy-21-methoxy-11β-[4-N,N-dimethylaminophenyl]-19-norpregna-4,9-diene-3,20-dione is dissolved at between 0° C.-40° C. in 1-50 times larger amount of a solvent selected from, cyclohexane, acetonitrile ethyl acetate, acetone and methanol, and mixture thereof, then it is stirred at between −20° C.-40° C. and the precipitated crystals are filtered, washed and dried;
wherein the crystalline anhydrate Form II of 17α-acetoxy-21-methoxy-11β-[4-N,N-dimethylaminophenyl]-19-norpregna-4,9-diene-3,20-dione is characterized in that it provides one or more of:
   a) a characteristic X-ray powder diffractions with peaks at 6.8, 11.0, 11.6, 14.9, 19.1±0.2 [°] 2θ;
   b) a characteristic FT Raman absorption bands at 3054, 2963, 2850, 1604, 1195, 1159±4 cm$^{-1}$; and
   c) a $^{13}$C solid-state NMR spectrum comprising characteristic resonances at 196.7, 172.4, 169.3, 20.7, 20.1, 17.7±0.1 ppm.

6. The process according to claim 5 wherein the amorphous 17α-acetoxy-21-methoxy-11β-[4-N,N-dimethylaminophenyl]-19-norpregna-4,9-diene-3,20-dione is dissolved in 2-10 times larger amount of the solvent.

7. The process according to claim 5 wherein the solvent is selected from: cyclohexane, ethyl-acetate, acetone, or acetonitrile.

8. The process according to claim 5 wherein the amorphous form of 17α-acetoxy-21-methoxy-11β-[4-N,N-dimethylaminophenyl]-19-norpregna-4,9-diene-3,20-dione is dissolved at between 20° C.-30° C.

9. The process according to claim 5 wherein the solution is stirred at between −5° C.-25° C.

* * * * *

UNITED STATES PATENT AND TRADEMARK OFFICE
CERTIFICATE OF CORRECTION

PATENT NO. : 9,221,870 B2
APPLICATION NO. : 13/387783
DATED : December 29, 2015
INVENTOR(S) : Balazs et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 104 days.

Signed and Sealed this
Twelfth Day of July, 2016

Michelle K. Lee
*Director of the United States Patent and Trademark Office*